United States Patent
Grone et al.

(10) Patent No.: US 6,810,204 B2
(45) Date of Patent: Oct. 26, 2004

(54) LOW PROFILE VAPORIZER

(75) Inventors: Ralf Grone, Boulder, CO (US); Christopher Bryan Schmidt, Aurora, CO (US); Debra Park, Mesa, AZ (US); Mengtao Pete He, Scottsdale, AZ (US); Kristopher J. Stathakis, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/666,659

(22) Filed: Sep. 18, 2003

(65) Prior Publication Data

US 2004/0057706 A1 Mar. 25, 2004

Related U.S. Application Data

(63) Continuation of application No. 10/074,529, filed on Feb. 12, 2002, now Pat. No. 6,714,725.

(51) Int. Cl.[7] .................................................. F24F 6/00
(52) U.S. Cl. ....................................... 392/392; 392/390
(58) Field of Search ................................. 392/386, 390, 392/392, 394, 395; 239/44, 45, 50

(56) References Cited

U.S. PATENT DOCUMENTS

| 4,293,173 A | 10/1981 | Tricca |
| 4,530,556 A | 7/1985 | Bonus |
| 4,718,856 A | 1/1988 | Pinkerton et al. |
| 4,731,520 A | 3/1988 | Glucksman et al. |
| 4,795,883 A | 1/1989 | Glucksman et al. |
| 4,804,821 A | 2/1989 | Glucksman |
| 4,849,606 A | 7/1989 | Martens, III et al. |
| 5,004,435 A | 4/1991 | Jammet |
| 5,111,477 A | 5/1992 | Muderlak et al. |
| 5,136,684 A | 8/1992 | Lonker et al. |
| 5,222,186 A | 6/1993 | Schimanski et al. |
| 5,375,728 A | 12/1994 | West |
| 5,465,198 A | 11/1995 | Kellogg |
| 5,522,008 A | 5/1996 | Bernard |
| 5,574,821 A | 11/1996 | Babasade |
| 5,647,052 A | 7/1997 | Patel et al. |
| 5,937,140 A | 8/1999 | Leonard et al. |
| 5,967,503 A | 11/1999 | Martin et al. |
| 6,044,202 A | 3/2000 | Junkel |
| 6,097,881 A | 8/2000 | DeWitt et al. |
| 6,104,866 A | 8/2000 | DeWitt et al. |
| 6,123,935 A | 9/2000 | Wefler et al. |
| 6,141,496 A | 10/2000 | Sundberg et al. |
| 6,289,176 B1 | 9/2001 | Martter et al. |
| 2001/0053283 A1 | 12/2001 | Levine et al. |

FOREIGN PATENT DOCUMENTS

WO    WO 01/93919    12/2001

OTHER PUBLICATIONS

Brochure–"Decora Devices," by Leviton, date unknown, Section A, pp. A1–A36.
Copy of PCT Written Opinion issued Mar. 5, 2004 for International Application No. PCT/US03/04082, International Filing Date Feb. 12, 2003, 4 pages.

*Primary Examiner*—Sang Paik
(74) *Attorney, Agent, or Firm*—Snell & Wilmer L.LP.

(57) ABSTRACT

A vapor dispensing device is provided which is less noticeable as a dispensing device to observers of the device. For example, in this context, the dispensing device may have the general appearance of a standard electrical wall outlet and have the ability to use the outlets into which the dispensing device is plugged.

7 Claims, 3 Drawing Sheets

LOW PROFILE VAPORIZER

CROSS-REFERENCE TO RELATED APPLICATIONS

This application is a continuation of U.S. patent application Ser. No. 10/074,529 entitled "Vapor-Dispensing Device," filed Feb. 12, 2002, Now U.S. Pat. No. 6,714,725, and is incorporated herein by reference.

FIELD OF INVENTION

This invention generally relates to vapor-dispensing devices, and more particularly, to a vapor-dispensing device with improved features.

BACKGROUND OF THE INVENTION

In general, vapor-dispensing products typically include a reservoir and a transport system from which fragrance or other volatizable materials are evaporated into the surrounding air. Generally, these systems require multiple, awkward components. For example, in some systems, the liquid is evaporated into the environment by transport from a separate reservoir bottle inserted into the housing via a wick material partially immersed in the liquid from a protruding housing which plugs into a wall outlet. In such a system, in general, the liquid is transported through the wick by capillary action.

In such devices, the heating element delivers kinetic energy to molecules of the liquid as contained in the wick, thereby increasing the rate of evaporation to obtain higher fragrance intensity and uniform delivery density over time. As mentioned above, in such units, a plug unit is plugged onto a conventional electrical outlet, thereby causing the heating unit to heat the liquid and vaporized liquid that have been drawn up into the wick. The wick and/or bottle unit containing the wick are suitably configured to such that the wick material is placed, when completely assembled, in proximity to the heating element.

However, while devices so configured typically ensure effective vaporization of the liquid to be dispensed, various difficulties can be encountered through use of the devices. For example, one of these difficulties is that the wick may become damaged either during insertion, use and/or removal of the wick containing reservoir (e.g., bottle). For example, during insertion and/or removal of the reservoir the wick may be caused to contact the heating element. Furthermore, movement of the reservoir relative to the housing during use or otherwise may give rise to deleterious or disadvantageous interactions between the wick and, for example, the heating unit. With such systems, particularly when used in a wick containing vaporizer, the wick may be damaged by being crushed or bent by careless interconnection, or be overheated by contact with the heating element during operation, due to instability and improper positioning of the wick material relative to the heating element. This same instability and improper positioning may cause uneven heating of the wick, result in diminished evaporative performance and consumer frustration.

Additionally, other disadvantages with prior art vapor dispensers result from the protruding nature of the device. For example, the unit itself may be inherently instable due to its being affixed at a relatively small point, yet extending a relatively significant distance from the wall outlet. Moreover, the protruding nature often causes the device to be more noticeable to people in the vicinity of the device. Thus, it may be less aesthetically pleasing. This likewise can be disadvantageous as children may be more likely to see the dispenser, and therefore, more likely to attempt to play with and/or remove the device. Further still, because the device is more noticeable, attention may be drawn to it. The same may prove embarrassing to the user of the dispenser as there may be negative connotations associated with "needing" a dispenser, i.e., the presence of an air freshener might imply one is trying to cover an unpleasant odor.

An even further disadvantage of known vapor dispensers is that when plugged into wall outlets, the ability to use the electrical outlets into which it is plugged is reduced or eliminated by the dispenser urging or blocking the outlets. While various dispensers have been developed which maintain the ability to plug other devices into the outlet while the dispenser is plugged in, such dispensers still suffer in that they are conspicuous and/or impede or eliminate the ability to use the wall outlet into which it is plugged.

Thus, there exists a need for a vaporizer which is less noticeable to observers of the device, provides improved features such as the ability to use electrical outlets into which it is plugged and/or has improved stability, more uniform delivery densities and/or vapor dispensation capabilities.

SUMMARY OF THE INVENTION

While the way in which the present invention addresses the disadvantages of the prior art will be discussed in greater detail below, in general, the present invention provides for a vapor dispenser which offers significant advantages to the user of the device which the prior art does not address.

For example, in accordance with various embodiments of the present invention, a vapor dispensing device is provided which is less noticeable as a vapor dispensing device. For example, in this context, in an illustrative embodiment of the present invention, the dispenser has the general appearance of a standard electrical wall outlet as well as including the ability to use the outlets into which the dispenser is plugged.

BRIEF DESCRIPTION OF THE DRAWINGS

The subject matter of the present invention is particularly pointed out and distinctly claimed in the concluding portion of the specification. A more complete understanding of the present invention, however, may best be obtained by referring to the detailed description and claims in connection with the drawing figures, wherein:

DETAILED DESCRIPTION

The following description is of exemplary embodiment of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth in the appended claims. For example, in the context of the present invention the method and apparatus hereof find particular use in connection with air freshening vaporizer systems. However, generally speaking, various volatizable materials exist (e.g., insect repellants, deodorizers, sanitizers or the like), and any number of such materials may be suitable for use in accordance with the present invention.

Figure 1:
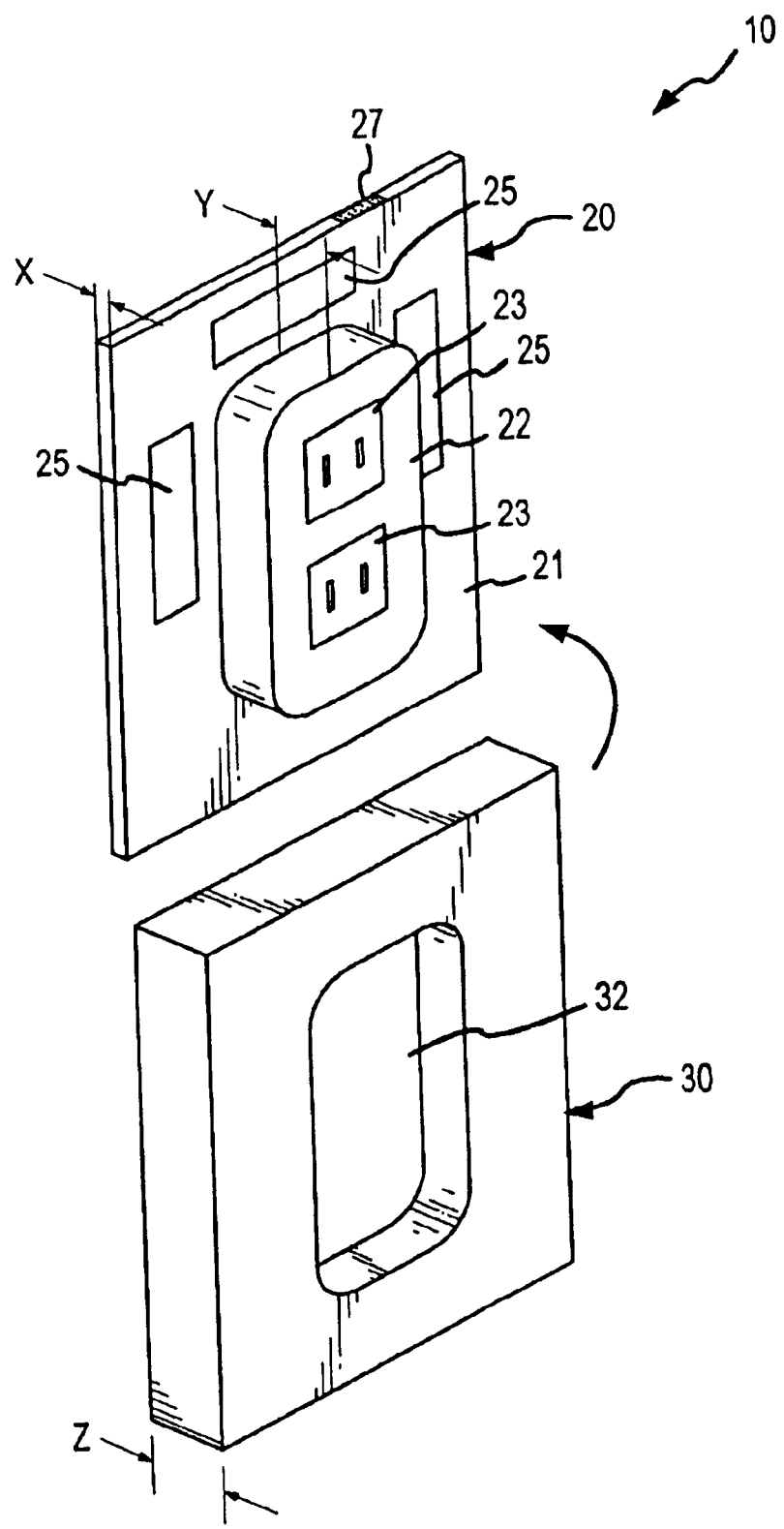
FIG. 1 is a perspective view of a vaporizer base and refill unit prior to assembly in accordance with an exemplary embodiment of the present invention.
Figure 2:
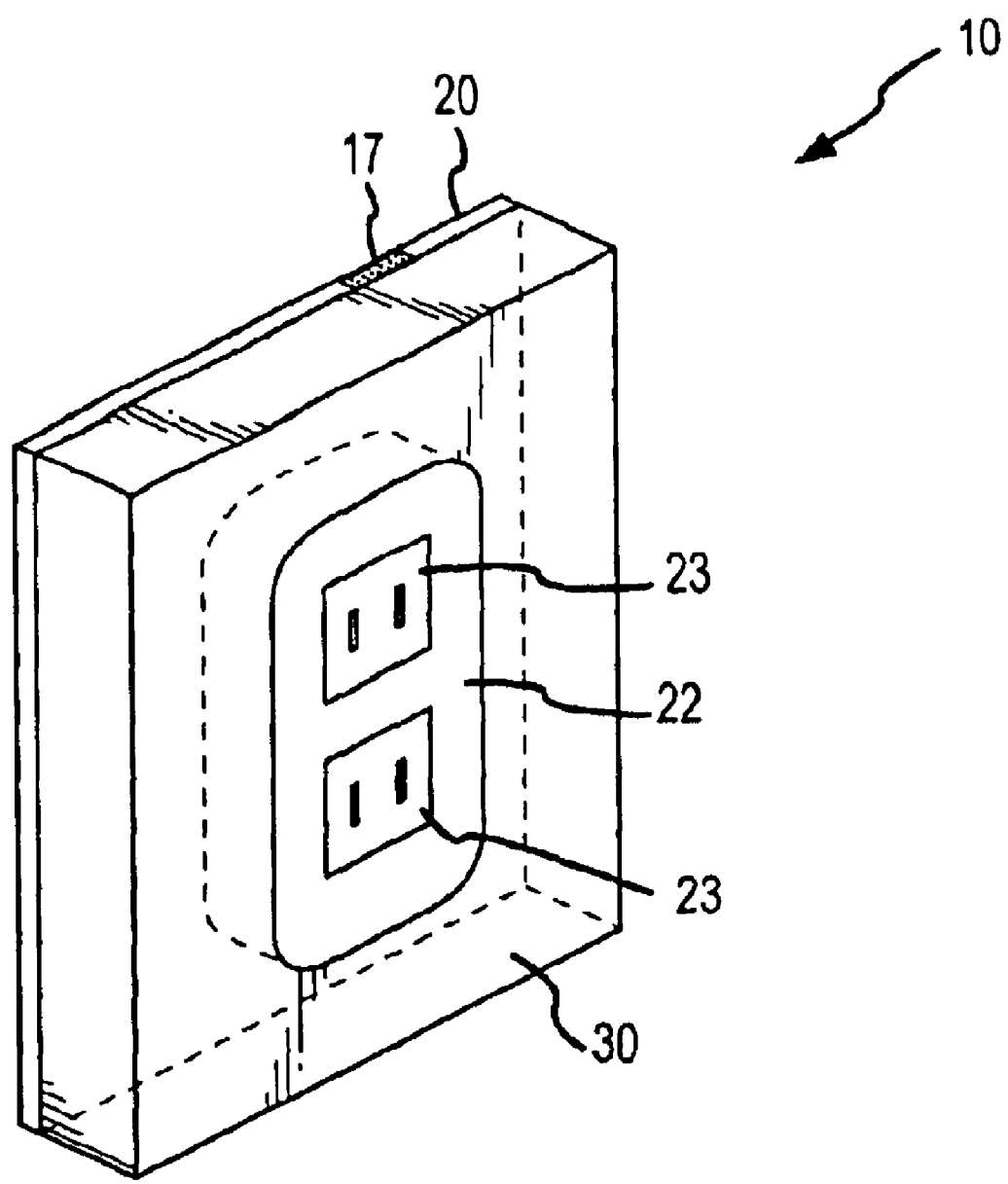
FIG. 2 is a perspective view of the assembled vaporizer base and refill unit of FIG. 2.
Figure 3:
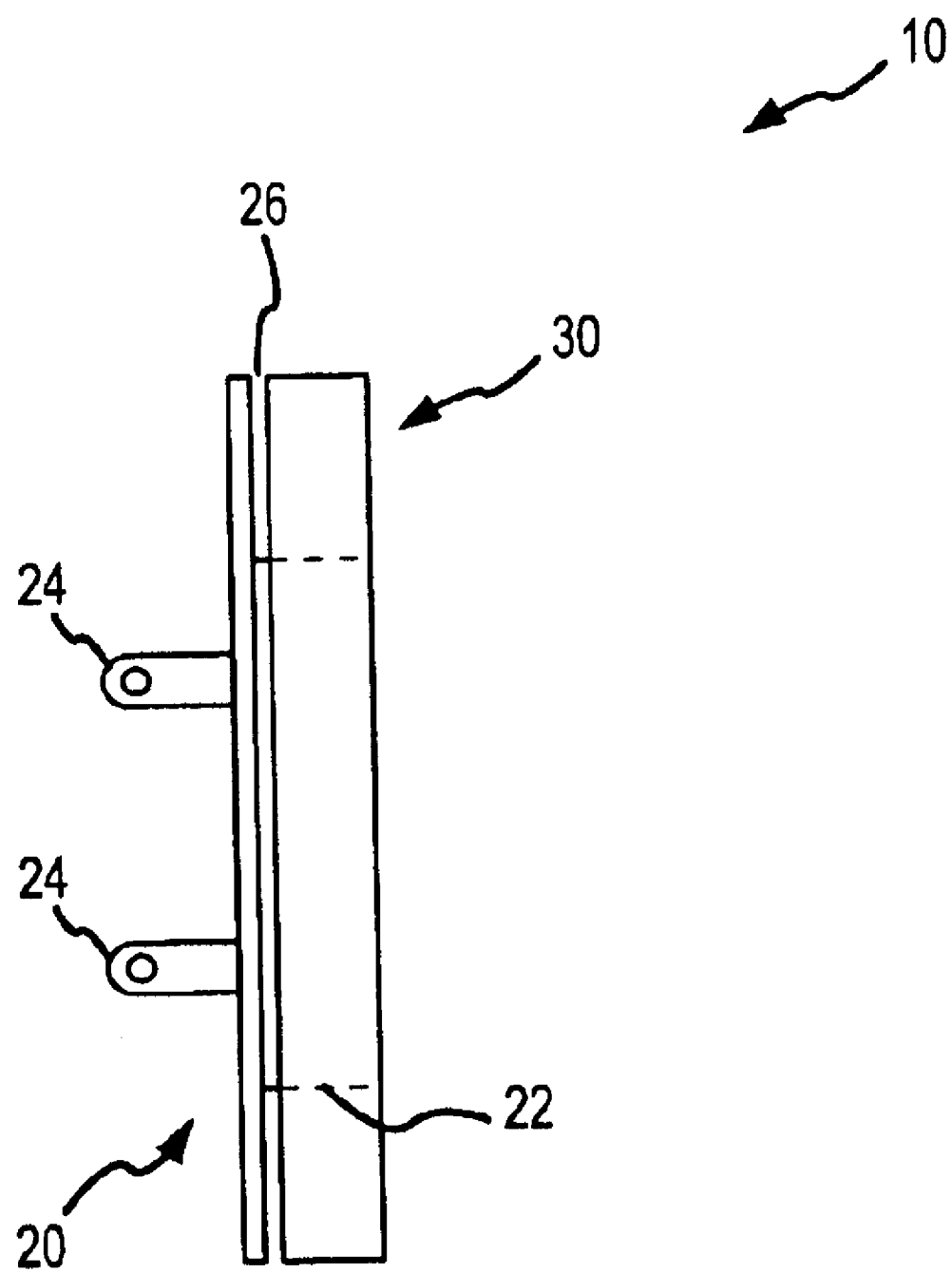
FIG. 3 is a side view of the assembled vaporizer base and refill unit of FIG. 2.

That being said, with reference to FIGS. 1–3, an exemplary embodiment of the present invention is illustrated. In this embodiment, vapor dispenser 10 suitably comprises a first structure 20 and a second structure 30 which suitably interconnect in an assembled form in a substantially seamless manner generally mimicing a standard wall outlet plate, which, in accordance with various aspects of the present invention, makes dispenser 10 less noticeable to observers or those in the vicinity of dispenser 10. In this exemplary embodiment, first structure 20 is a base upon which second structure 30, in the form of a fragrance refill unit, is affixed.

Briefly, however, it is worth noting that in accordance with various alternative embodiments of the present invention, dispenser 10 may comprise any number of structures, including comprising a single structure. For example while the presently described embodiment comprises first structure 20 which serves to facilitate connection to the wall outlet and heating of the material provided by second structure 30, in various other embodiments, first structure 20 and second structure 30 might have different roles, i.e., they may act cooperatively to provide heat for volatilization and/or fragrance and heating elements may be reversed on the structures. Further still, alternatively, dispenser 10 may comprise a single, unitary structure with all vaporization elements integrated into dispenser 10. Additionally, as described in additional detail below, in accordance with various aspects of the present invention, dispenser 10 is suitably configured such that the ability to use the outlets into which dispenser 10 is plugged is maintained when dispenser 10 is plugged in.

Now with reference to an exemplary embodiment such as that shown in FIG. 2, first structure 20 suitably comprises a rectangular shaped base plate 21, from which extends an outlet structure 22 substantially centrally located on base plate 21. In the present exemplary embodiment, as mentioned above, base plate 21 is configured with substantially the same shape and size (typically rectangular) as a standard wall outlet plate. Preferably, base plate 21 has a narrow thickness X which aids in maintaining a discrete, less noticeable nature of dispenser 10. In its various embodiments, however, it should be appreciated that base plate 21 can be configured in any number of sizes and shapes (e.g., round, rectangular, triangular, etc.) and any number of thicknesses X.

As mentioned above, outlet structure 22 extends from a substantially central location of base plate 21. Generally speaking, outlet structure 22 is a block-like configuration of built up material for receiving second structure 30. Additionally, in accordance with various embodiments of the present invention, outlet structure 22 surrounds electrical outlets 23, which are preferably located in a substantially similar location as the outlets of a standard wall outlet and facilitate the interconnection of first structure 20 and second structure 30, as well as, in various instances, the ability to provide power to other devices through outlets 23. For example, in accordance with various embodiments of the present invention, outlets 23 correspond to look like and perform like a standard wall outlet. Additionally, momentarily it should be appreciated that outlets 23 can be configured in accordance with any outlet configuration. That is, outlets 23 may be two prong, three prong or any other configuration.

In the present exemplary embodiment, outlet structure 22 extends from base plate 21, a distance Y. Similar to base plate thickness X, preferably, distance Y is relatively small such that the low-profile nature of dispenser 10, and therefore, low noticeability is maintained. Of course, similar to thickness X of base plate 21, distance Y is variable depending on the particular application of dispenser 10 and varying distances may be used and still fall in within the ambit of the appended claims.

Similarly, outlet structure 22 may be suitably configured in any number of shapes and likewise may comprise any number of distinct projecting structures. For example, in the presently described embodiment, outlet structure 22 comprises one structure which surrounds both outlets 23 and has a substantially rectangular shape with rounded corners. However, outlet structure 22 may also comprise many variants of shapes. For example, outlet structure 22 may be suitably configured with an "hour-glass," "circular," or "triangular" configuration or the like. Similarly, rather than outlet structure comprising one unitary structure surrounding both outlets 23, outlet structure can comprise two or more separate and distinct structures, each surrounding another outlet. Likewise, those separate structures themselves can have any number of configurations and shapes. Moreover, outlet structure 22, as shown in the illustrated exemplary embodiment, need not have any outlets 23 but rather may simply cover the wall outlets.

In accordance with various aspects of the present embodiment, first structure 20 further comprises one or more plugs 24 which extend from the back of base plate 21. Again, momentarily, it should be appreciated that, like outlets 23, plugs 24 can take any number of configurations (e.g., two prong, three prong, etc.) One potential advantage of this is that plugs 24 and outlets 23 may have different configurations, and dispenser 10 may act as an adapter for different styles of plug and outlet configurations. With particular reference to FIG. 3, the presently described embodiment has two sets of plugs 24 which are configured such that both plugs 24 can be inserted into a standard wall outlet. Advantageously, in accordance with various aspects of the present invention either or both of plugs 24, provide power to dispenser 10, and its heating elements, for use in vaporizing volatizable material from second structure 30. Additionally, in this embodiment, dual plugs 24 provide improved stability of dispenser 10 when placed in the wall outlet.

However, it should be appreciated that in accordance with various alternative embodiments of the present invention, for dispensers 10 having multiple plugs 24, only one of plugs 24 may actually provide current/power to dispenser 10, thus providing improved stability and, moreover, safety through covering the non-powering outlet. Of course, in still other alternative embodiments, dispenser 10 may only have one plug 24.

As briefly mentioned above, dispenser 10 may be suitably configured such that the ability to use the outlets into which dispenser 10 is plugged is maintained when dispenser 10 is plugged in. For example, in the various embodiments of dispenser 10, outlets 23 may be suitably electrically connected to plugs 24, thereby providing electrical capability to outlets 23. Thus, using operating outlets 23 thereby increases the inconspicuousness of dispenser 10, for example, by allowing other devices (e.g., lamps, televisions, clocks, etc.) to be plugged into the same outlet, maintaining the illusion that dispenser 10 is merely a typical outlet.

With reference now back to FIG. 2, in the presently described non-limiting embodiment, first structure 20 further comprises a heating element 25 which suitably assists in vaporizing the volatizable material from second structure 30. In this embodiment, heating element 25 comprises a resistance-type heating element, though generally speaking, any mechanism which assists in volatizing the material from second structure 30 may, typically through kinetic energy, be a "heating element". Additionally, momentarily, it should be noted, that in various alternative embodiments of the present invention, dispenser 10 may be a "passive" vaporizer. Stated otherwise, the material of second structure 30 may volatize merely by exposure to ambient conditions (e.g., room temperature). Thus, no heating element 25 may be required.

In the presently described embodiment, heating elements 25 are preferably located on base plate 21. In such a manner, contact area between second structure 30 and first structure 20 is suitably optimized when dispenser 10 is assembled, thereby increasing the volatilization mechanism. However, the location of heating elements 25 of the presently described embodiment are merely for illustrative purposes and heating elements 25 may also be placed in any number of locations on dispenser 10. For example, in addition to and/or in lieu of placing heating elements 25 on base plate 21, heating elements may be suitably incorporated into outlet structure 22 or other structures not discussed in detail herein. In accordance with various optional aspects of the present invention, heating element 25 may be suitably configured with various additional features which serve to improve the functionality of dispenser 10. For example, in accordance with one aspect of the present invention, heating elements 25 may suitably be configured such that they can be switched back and forth from and ON and OFF positions. For example, the ON and OFF positions may be manipulated through the use of a switch 27, such as a sliding tab, on dispenser 10.

Additionally (or alternatively), heating elements 25 may be suitably configured to be adjustable to varying temperatures. In accordance with various aspects of the present invention, switch 27 may also be suitably configured to control the varying temperature of heating element 25. Thus, the functionality of dispenser 10 can be improved. For example, in the case of a fragrance dispenser, when fragrance is not needed, dispenser 10 can be turned off so that dispensation of fragrance is reduced and/or stopped. Similarly, dispensers having variable temperature control can provide the ability to increase or decrease the amount of fragrance dispensed depending on the intensity and strength of heat provided by heating element 25, user desired performance, room size and the like.

As briefly mentioned above, vapor dispenser 10 may comprise second structure 30. Generally speaking, second structure 30 comprises any suitable delivery mechanism for dispensation of a volatizable material. For example, second structure 30 may be configured as a liquid filled reservoir which is functionally similar to the reservoir bottles of now known vaporizer refill bottles. In such configurations, second structure 30 has a hollow section filled with, for example, a scented oil which is vaporized from second structure 30. The actual vaporization of the volatizable material from second structure 30 can likewise occur in any number of manners. For example, such mechanisms may suitably include, wicking of the material from second structure 30 through a porous material such as graphite, porous plastic or fibrous materials.

However, alternatively, second structure 30 may also comprise other material delivery systems such as, for example, gel and/or membrane type fragrance dispensers. In such cases, the volatizable material might be in a "gel" and/or semi-permeable solid form which dispenses through mechanisms such as sublimation. The same can prove particularly useful for dispenser 10 having a single structure configuration. Thus, it should be appreciated that any fragrance delivery mechanism now known or as yet unknown in the art can suitably be configured to be used in the present invention.

That being said, in accordance with the presently described illustrative embodiment, second structure 30 is suitably configured base shape and size such that it can be assembled to first structure 20 in a manner which facilitates the minimizing of the likelihood of being noticed by those in the vicinity of dispenser 10. For example, in the present exemplary embodiment, second structure 30 has a substantially rectangular shape corresponding to first structure 20 (similar to a standard wall outlet plate). Additionally, the presently described embodiment suitably exhibits improved stability, and/or which facilitates the interaction of heating elements 25 (to the extent they are included in dispenser 10) with second structure 30.

In this embodiment, second structure 30 further comprises an aperture 32 to facilitate connection of second structure 30 to first structure 20. In the present embodiment, aperture 32 extends all of the way through second structure 30, though in various alternate embodiments, to facilitate the above-mentioned interconnection, the aperture may only extend partially through second structure 30 therethrough. Preferably, aperture 32 is of substantially the same size as outlet structure 22. Moreover, preferably, second structure 30 has a thickness Z which is substantially similar to outlet structure 22. Thus, in accordance with various embodiments of the present invention and using FIGS. 1 and 2, to illustrate assembly of this embodiment of vapor dispenser 10, second structure 30 can be placed over outlet structure 22 to form the assembled vapor dispenser 10 of FIG. 3.

Such configurations of first structure 20 and second structure 30 thus provide advantages over the prior art through being less noticeable. For example, in the illustrated embodiment, because distance Y of outlet structure 22 and thickness Z of second structure 30 are substantially similar/less noticeable, the outer face of dispenser 10 is substantially seamless and therefore less notable. Additionally, in the presently described embodiment, because second structure 30 and first structure 20 have similar lengths and widths, in this case substantially similar to a standard wall outlet, dispenser 10 is less noticeable to the casual observer.

In accordance with another aspect of the present invention, dispenser 10 and particularly the assembly of first structure 20 and second structure 30 suitably provide for additional improved performance characteristics. For example, with reference particularly to FIG. 3, when second structure 30 and base plate 22 are assembled, second structure 30 and/or first structure 20 are configured such that an air channel is provided between first structure 20 and second structure 30. In accordance with various aspects of this embodiment, air channel 26 suitably allows the passage of air, as it heats, to pass over the dispensing mechanism of second structure 30 and further enhance the dispensation of the volatizable material contained within second structure 30. In accordance with various alternative aspects of the present invention, second structure 30 and/or first structure 20 may also be configured with various mechanisms for improving dispensation capabilities. For example, in accordance with various embodiments of the present invention, and depending on the type of delivery mechanism second structure 30 employs, second structure 30 may be configured with vents, air passages and/or projecting wick materials.

Similarly, dispenser 10 may configured with a fan or blower to facilitate the flow of air over the dispensing mechanism.

Last, various principles of the invention have been described in illustrative embodiments. However, many combinations and modifications of the above-described structures, arrangements, proportions, elements, materials and components, used in the practice of the invention, in addition to those not specifically described, may be varied and particularly adapted to specific environments and operating requirements without departing from those principles.

We claim:

1. A vapor dispensing device configured to contain a vaporizable material, comprising a first structure configured to be inserted into a wall outlet having substantially the same dimensions of a wall outlet plate, further having an outwardly extending outlet structure having a thickness, a removable second structure comprising a bottle having an aperture configured in substantially the same size as said outlet structure such that said second structure can be attached to said first structure.

2. A vapor dispensing device in accordance with claim 1, wherein said second structure and said first structure, when assembled, resemble a wall outlet.

3. A vapor dispensing device in accordance with claim 1, wherein said first structure has a first plug for inserting into a wall outlet.

4. A vapor dispensing device in accordance with claim 3, wherein said first structure further comprises a second plug.

5. A vapor dispensing device in accordance with claim 4, wherein one of said first plug and said second plug provide power to the vapor dispensing device.

6. A vapor dispensing device in accordance with claim 4, wherein both of said first plug and said second plug provide power to the vapor dispensing device.

7. A vapor dispensing device in accordance with claim 1, further comprising at least one outlet on an outer face of the vapor dispensing device.

* * * * *